(12) United States Patent
Chen et al.

(10) Patent No.: US 10,373,701 B2
(45) Date of Patent: Aug. 6, 2019

(54) METHODS AND APPARATUSES FOR CREATING A STATISTICAL AVERAGE MODEL OF AN ENAMEL-DENTINE JUNCTION

(71) Applicant: Nuctech Company Limited, Haidian District, Beijing (CN)

(72) Inventors: Zhiqiang Chen, Beijing (CN); Yuanjing Li, Beijing (CN); Li Zhang, Beijing (CN); Ziran Zhao, Beijing (CN); Jianping Gu, Beijing (CN); Shuo Wang, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 1121 days.

(21) Appl. No.: 14/540,457

(22) Filed: Nov. 13, 2014

(65) Prior Publication Data

US 2015/0220683 A1    Aug. 6, 2015

(30) Foreign Application Priority Data

Nov. 18, 2013    (CN) .......................... 2013 1 0574340

(51) Int. Cl.
    *G16B 5/00*      (2019.01)
    *G06F 17/18*     (2006.01)
    *G06K 9/62*      (2006.01)
    *G06T 17/20*     (2006.01)

(52) U.S. Cl.
    CPC ............... *G16B 5/00* (2019.02); *G06F 17/18* (2013.01); *G06K 9/6209* (2013.01); *G06T 17/20* (2013.01); *G06K 2209/055* (2013.01); *G06T 2210/41* (2013.01)

(58) Field of Classification Search
    None
    See application file for complete search history.

(56) References Cited

U.S. PATENT DOCUMENTS

| 2011/0212419 | A1* | 9/2011 | Schweiger | ......... A61C 13/0004 433/202.1 |
| 2012/0330636 | A1* | 12/2012 | Albou | ..................... G06F 19/16 703/12 |
| 2013/0308843 | A1* | 11/2013 | Tank | ..................... A61C 19/04 382/128 |

OTHER PUBLICATIONS

Kiyoshi Tajima et "alThree-dimensional finite element modeling from CT images of tooth and its validation" (Year: 2009).*
Tajima, K. et al., "Three-dimensional finite element modeling from CT images of tooth and its validation", Dental Materials Journal, 28(2): 219-226, 2009.

(Continued)

*Primary Examiner* — Timothy A Mudrick
*Assistant Examiner* — Abdou Seye
(74) *Attorney, Agent, or Firm* — Merchant & Gould P.C.

(57) ABSTRACT

Disclosed is method and apparatus for creating a statistical average model of an enamel-dentine junction. The method includes steps of acquiring CT image data of a tooth; segmenting the CT image data to obtain a surface of an enamel-dentine junction; segmenting the obtained surface using a curvature-based clustering algorithm to remove a bottom of the enamel-dentine junction; spherical-parameterizing, by means of spherical harmonic analysis, the surface of the enamel-dentine junction after removal of the bottom; and aligning different samples of the tooth to obtain a statistical average model.

9 Claims, 7 Drawing Sheets

(56) References Cited

OTHER PUBLICATIONS

Shen, L. et al., "Modeling Three-Dimensional Morphological Structures Using Spherical Harmonics", The Society for the Study of Evolution, 64(4): 1003-1016, 2009.
Shen, L. et al., "Spherical mapping for processing of 3D closed surfaces", Image and Vision Computing, 24: 743-761, 2006.
Shen, L. et al., Efficient Registration of 3D SPHARM Surfaces:, Fourth Canadian Conferences on Computer and Robot Vision, IEEE, pp. 81-88, 2007.
Rahimi, A. et al., "Computer Methods in Biomechanics and Biomedical Engineering", Computer Methods in Biomechanics and Biomedical Engineering, 8(3): 167-176, 2005.
Yokoya, N. et al., "Range Image Segmentation Based on Differential Geometry: A Hybrid Approach", IEEE Transactions on Pattern Analysis and Machine Intelligence, 11(6): 643-649, 1989.
Chen, G. et al., "Spectral Curvature Clustering (SCC)", International Journal of Computer Vision, 81(3): 317-330, 2008.
Extended European Search Report for corresponding European Patent Application No. 14193154.3 dated Mar. 25, 2015.
Olejniczak et al. "Quantification of dentine shape in anthropoid primates", Annals of Anatomy Journal, 2004, 186: 479-485.
Smith et al. "Modern human molar enamel thickness and enamel-dentine junction shape", Archives of Oral Biology, 2006, 51: 974-995.
Fonseca et al. "Radiodensity of enamel and dentin of human, bovine and swine teeth", Biology, 2004, 49: 919-922.
Corruccini "The Dentinoenamel Junction in Primates", International Journal of Primatology, 1987, 8(2): 99-114.
Kraus "Morphologic Relationships Between Enamel and Dentin Surfaces of Lower First Molar Teeth", Journal of Dental Research, 1952, 31(2): 248-256.
Bazos et al. "Bio-Emulation: Biomimetically Emulating Nature Utilizing a Histo-Anatomic Approach; Structural Analysis", The European Journal of Esthetic Dentistry, vol. 6(1): 8-19, 2001.
Wang Xiao-Jang et al. "The feasibility study of three-dimensional reconstruction of surface morphology of the enamel dentinal junction by cone beam CT", Peking University Health Science Center, Beijing, 2012.
Shen et al., "Spherical Mapping for Processing of 3-D Closed Surfaces", Computer and Information Science, University of Massachusetts Dartmouth, 24(7): 743-761, 2006.
Taubin, Estimating the Tensor of Curvature of a Surface from a Polyhedral Approximation:, In: WEL Grimson ed. Proceedings of the Fifth International conference on Computer Version[C], Los Alamitos: IEEE Computer Society Press, 1995: 902-907.
Shen et al., "Efficient Registration of 3D SPHARM Surfaces", In: 4th Canadian Conf. on Computer & Robot Vision. (2007) 81-88.

* cited by examiner

METHODS AND APPARATUSES FOR CREATING A STATISTICAL AVERAGE MODEL OF AN ENAMEL-DENTINE JUNCTION

This application claims benefit of Serial No. 201310574340.0, filed 18 Nov. 2013 in China and which application is incorporated herein by reference. A claim of priority is made to the above disclosed application.

TECHNICAL FIELD

The present disclosure relates to medical image processing, and more particularly, to methods and apparatuses for creating a statistical average model of an enamel-dentine junction.

BACKGROUND

Aesthetic effects of natural tooth color and semi-transparent gradual change are produced by superposing dental enamel and dentine with an interface of enamel-dentine junction. To solve the problem that beauty and strength cannot be guaranteed at the same time for pure-zirconia ceramic crown of molar tooth, one effective approach is to develop a type of zirconia ceramic which has a gradient gradual change in optical color and can be processed with Computer Aided Design (CAD)/Computer Aided Manufacturing (CAM), by simulating structure and optical characteristics of the tooth. Basis for such structure simulation is to learn a complete modality of the curved surface of the enamel-dentine junction. In the research of the enamel-dentine junction modality, Document 1 (Anthony J. Olejniczak, Lawrence B, et al. Quantification of dentine shape in anthropoid primates[J]. Ann Anat, 2004, 186: 479-485) and Document 2 (Smith T. M, Olejniczak A. J, Reid D. J, et al. Modern human molar enamel thickness and enamel-dentine junction shape[J]. Archives of Oral Biology, 2006, 51: 974-995) study a modality of the enamel-dentine junction in some axial plane of the tooth, and the obtained enamel-dentine junction is a line other than a plane. Document 3 (Rodrigo Borges Fonseca, Francisco Haiter-Neto, Alfredo J. Fernandes-Neto, et al. Radiodensity of enamel and dentin of human, bovine and swine teeth[J]. Archives of Oral Biology, 2004, 49:919-922) acquires a complete curved surface of the enamel-dentine junction through Micro-CT (Computed Tomography). Document 4 (Robert S, Corruceini. The Dentinoenamel Junction in Primates[J]. International Journal of Primatology, 1987, 8(2): 99-114), Document 5 (Bertram S, Kraus. Morphologic relationships between enamel and dentin surfaces of lower first molar teeth[J]. J. D. Res, 1952, 31(2):248-256) and Document 6 (Panaghlotis Bazos, Pascal Magne. Bio-emulation: biomimetically emulating nature utilizing a histo-anatomic approach; structural analysis[J]. The European journal of esthetic dentistry, 2011, 6(1): 8-19) acquire a complete curved surface of the enamel-dentine junction using a method of selectively removing enamel with acid demineralization. The two methods using Micro-CT and acid demineralization can be applied only on isolated teeth but not live natural teeth, because ray dose in Micro-CT is large, and the acid demineralization method is destructive. As a result, it is difficult to collect a number of samples required to establish an enamel-dentine junction database. Document 7 (Xiaojing Wang. Research on feasibility of creating 3D mortality of enamel-dentine junction surface with cone-beam CT[D]. Peking University Health Science Center, Beijing, 2012) can acquire the mortality of enamel-dentine junction surface without tooth damage by using cone-beam CT scanning in combination with image segmentation technology.

Document 8 (Kurbad A. Three-dimensionally layered ceramic blocks[J]. Int J Comput Dent, 2010, 13(4): 351-65) attempts to build a 3D laminated structure resembling a natural dental crown in a full-ceramic block. The ceramic block is structured so that the inner ceramic part emulates the optical characteristics of dentine, the outer ceramic part emulates the optical characteristics of enamel, and an interface between the two parts is cone-shaped. This can emulate, to some extent, semi-transparency and gradual change in color of natural crown, while it is inaccurate to assume the enamel-dentine junction as cone-shaped.

A statistical shape model is a model created from corresponding sets of mark points in surfaces of anatomic structures of interest in a single individual at different moments or between different individuals at the same moment. Creation of the statistical shape model is on the premise of acquisition of corresponding mark point sets between anatomic structures. Document 9 (Shen L, Makedon F S. Spherical mapping for processing of 3-D closed surfaces. Image and Vision Computing, 24(7): 743-761, 2006) proposes a Spherical Harmonic Description (SPHARM) which determines correspondence between structures through normalization of parametric space. Statistical modeling and analysis with SPHARM require that input grids should be genus-zero surfaces, i.e., the module should have a spherical topology. The enamel-dentine junction, however, is an interface between two different mineralized tissues of epithelium and extracellular matrix, and has an unclosed surface in a shell shape.

SUMMARY

There is a need for methods of creating a statistical average module that is applicable to an unclosed surface.

According to an aspect of the disclosure, a method for creating a statistical average model of an enamel-dentine junction is provided, comprising steps of: acquiring CT image data of a tooth; segmenting the CT image data to obtain a surface of an enamel-dentine junction; segmenting the obtained surface using a curvature-based clustering algorithm to remove a bottom of the enamel-dentine junction; spherical-parameterizing, by means of spherical harmonic analysis, the surface of the enamel-dentine junction after removal of the bottom; and aligning different samples of the tooth to obtain a statistical average model.

In an embodiment, the CT image data are segmented using the Level Set algorithm.

In another embodiment, the clustering algorithm comprises the K-Means algorithm.

In a further embodiment, the spherical-parameterization is performed using an optimized Control of Area and Length Distortions algorithm.

In an embodiment, the area and length distortion control algorithm is optimized by adding weights.

In an embodiment, the method further comprises: applying spherical harmonics Fourier expansion on the parameterized surface after the spherical-parameterization.

In an embodiment, the alignment is performed in a spherical coordinate system.

In an embodiment, the alignment is performed by means of the SPHARM Registration with Iterative Closest Point (SHREC) algorithm.

With the method for creating an average model of the present disclosure, it is possible to describe an object surface using spherical harmonics function in an unclosed surface, and establish correspondence of mark point sets between structures. Accordingly, in case of the cone-beam CT scanning samples of isolated teeth, a statistical average model describing the mortality of enamel-dentine junction surface can be created with any damage to the teeth.

BRIEF DESCRIPTION OF THE DRAWINGS

The above and other aspects of the present disclosure will be apparent and illustrated with reference to embodiments in the following. In figures.

DETAILED DESCRIPTION OF THE EMBODIMENTS

The particular embodiments of the disclosure are described below in details. It shall be noted that the embodiments herein are used for illustration only, but not limiting the disclosure. In the description below, a number of particular details are explained to provide a better understanding to the disclosure. However, it is apparent to those skilled in the art the disclosure can be implemented without these particular details. In other examples, well-known circuits, materials or methods are not described so as not to obscure the disclosure.

Throughout the specification, reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that figures here are for the purpose of illustration, and not necessarily drawn to scale. It should be appreciated that "connecting" or "coupling" a component to another component may mean that the component is directly connected or coupled to the other component, or there may be a component intervening between them. On the contrary, "directly connecting" or "directly coupling" a component to another component mans that there is no intervening component. Like reference signs refer to similar elements throughout the figures. The term "and/or" used herein means any and all combinations of one or more listed items.

Figure 1:
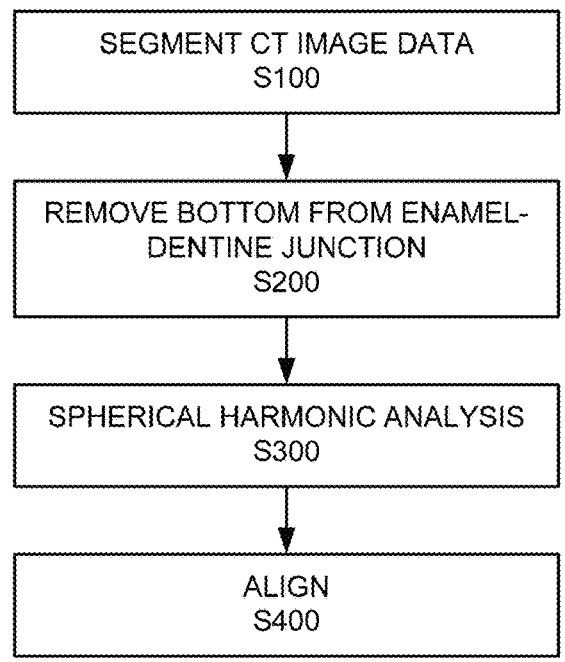
FIG. 1 illustrates a flowchart of a method embodiment according to the disclosure.
Figure 2:
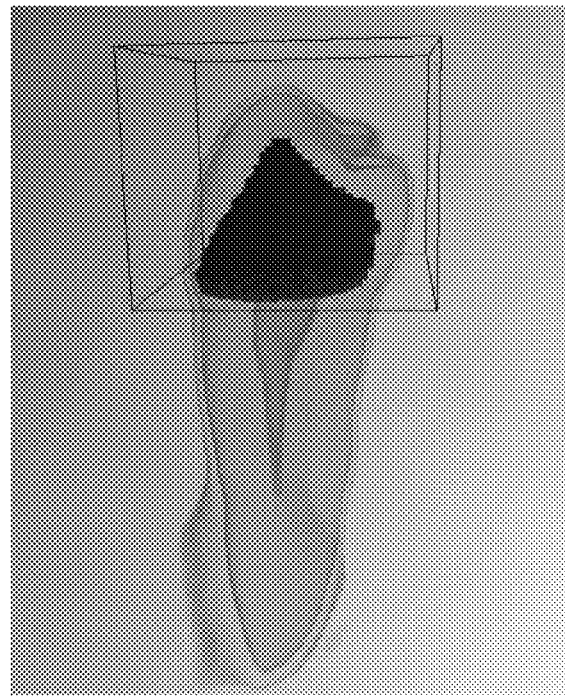
FIG. 2 illustrates a schematic diagram of a segmented surface of enamel-dentine junction according to a method embodiment of the disclosure.

FIG. 1 illustrates a flowchart of a method embodiment according to the disclosure.

After acquiring Computerized Tomography (CT) image data of a tooth, the CT image data are segmented at step S100 to remove enamel in the surface layer, and reconstruct a 3D mortality of the surface of an enamel-dentine junction. In an embodiment, the well-known Level Set algorithm based on Sparse Field may be used for the segmentation.

During the segmentation of the CT image, interception of the dentine with a cube in a region of interest will cause the enamel-dentine junction surface, which should have been opened, to become closed. However, if the bottom is included in acquiring the statistical average model of the enamel-dentine junction, accuracy for the modeling will be considerably reduced. In the embodiment of the present disclosure, it is required to segment out the bottom and any possible pulp cavity, and thus reduce influence of the bottom and pulp cavity during the creation of statistical average model.

After reconstructing the 3D mortality of the enamel-dentine junction surface, the bottom is separated from the enamel-dentine junction using a curvature-based clustering algorithm at step S200.

In an embodiment of the present disclosure, a triangular grid model is used to emulate the enamel-dentine junction surface. The triangular grid model M may be represented by a pair of linear sets:

$$M=(V,F)$$

$V=\{v_i:1 \leq i \leq n_V\}$ denotes a set of vertices, and $n_V$ is the number of vertices. $F=\{f_k:1 \leq k \leq n_F\}$ denotes a set of triangular patches, and is the number of triangular patches.

In order to implement the curvature-based clustering algorithm, it is necessary to compute normal vectors at the vertices of the triangular grid model, and compute curvatures at the vertices of the triangular grid model based on these normal vectors.

The normal vectors at the vertices may be computed as follows.

Assuming that a vertex of the triangular grid model is denoted as $v_i$, and a set of vertices except the vertex $v_i$ is denoted as $V^i$. A vertex $v_j$ is a neighbor point of $v_i$ if $v_j \in V^i$. The number of vertices in $V^i$ is denoted as $|V^i|$. A set of triangular patches including $v_i$ is denoted as $F^i$. $f_k$ is associated with $v_i$ if the triangular patch $f_k \in F^i$. The number of triangular patches in $F^i$ is denoted as $|F^i|$.

To reflect influence of the shape of the triangular patch on the normal vector at the vertex, the normal vector $N_{v_i}$ at the vertex $v_i$ is computed with Equation (1):

$$N_{v_i} = \frac{\sum_{f_k \in F^i} \gamma_k A_k N_{f_k}}{\left\| \sum_{f_k \in F^i} \gamma_k A_k N_{f_k} \right\|} \tag{1}$$

$\gamma_k$ is an interior angle of $f_k$ at the vertex $v_i$, Ak is an area of the triangular patch $f_k$, and $N_{f_k}$ is the normal vector of the triangular patch $f_k$ and is determined with Equation (2):

$$N_{f_k} = \frac{e_{i,j+1} \times e_{ij}}{\|e_{i,j+1} \times e_{ij}\|} = \frac{(v_i - v_{j+1}) \times (v_i - v_j)}{\|(v_i - v_{j+1}) \times (v_i - v_j)\|} \tag{2}$$

$e_{i,j+1}$ denotes a edge vector pointing from the vertex $v_{j+1}$ to the vertex $v_i$.

After computation of the normal vector at the vertex, the curvature at the vertex of the triangular grid is computed as follows.

A tangent plane at a vertex is first computed, and then vertices in the neighborhood of the vertex are projected onto the tangent plane. The normal vector $N_{v_i}$ at the vertex $v_i$ is, and a plane having the normal vector $N_{v_i}$ and passing the vertex $v_i$ is the tangent plane, denoted as $\langle N_{v_i} \rangle^\perp$, at the vertex $v_i$. A vertex $v_j$ in the neighborhood of the vertex $v_i$ is projected onto the tangent plane as $v_j^\perp$.

A unit tangent vector $T_{ij}$ of the vertex $v_i$ in the tangent plane $\langle N_{v_i} \rangle^\perp$ along a direction of $v_i v_j^\perp$ is:

$$T_{ij} = \frac{\langle N_{v_i}, v_j - v_i \rangle N_{vi} - (v_j - v_i)}{\|\langle N_{v_i}, v_j - v_i \rangle N_{vi} - (v_j - v_i)\|} \quad (3)$$

$\langle \rangle$ denotes a dot product of two vectors.

A symmetric matrix $M_{v_i}$ is computed with the unit tangent vector:

$$M_{v_i} = \sum_{v_j \in V^i} w_{ij} k_{ij} T_{ij} (T_{ij})^T = \begin{bmatrix} m_{v_i}^{11} & m_{v_i}^{12} & m_{v_i}^{13} \\ m_{v_i}^{21} & m_{v_i}^{22} & m_{v_i}^{23} \\ m_{v_i}^{31} & m_{v_i}^{32} & m_{v_i}^{33} \end{bmatrix} \quad (4)$$

$$w_{ij} = \frac{A_{f_k}}{\sum_{f_k \in F^i} A_{f_k}}$$

is a weight, $T_{ij}$ is the unit tangent vector at the vertex $v_i$, and $$k_{ij} = \frac{2\langle N_{v_i}, v_j - v_i \rangle}{\|v_j - v_i\|^2}$$

is a curvature at the vertex $v_i$ along a direction of $T_{ij}$.

The symmetric matrix $M_{v_i}$ has two eigenvalues $m_{v_i}^{11}$ and $m_{v_i}^{22}$. Document 10 (G. Taubin. Estimating the tensor of curvature of a surface from a polyhedral approximation[A]. In: WEL Grimson ed. Proceedings of the Fifth International Conference on Computer Version[C], Los Alamitos: IEEE Computer Society Press, 1995: 902-907) describes equations for solving the principal curvatures at the vertex $v_i$ based on the two eigenvalues:

$$k_{v_i}^1 = 3 m_{v_i}^{11} + 8 m_{v_i}^{22}$$

$$k_{v_i}^2 = 3 m_{v_i}^{22} + 8 m_{v_i}^{11} \quad (5)$$

As such, the principal curvature values $k_1$, $k_2$ and corresponding curvature directions $d_1$, $d_2$ can be obtained for each vertex of the triangular grid.

Figure 3:
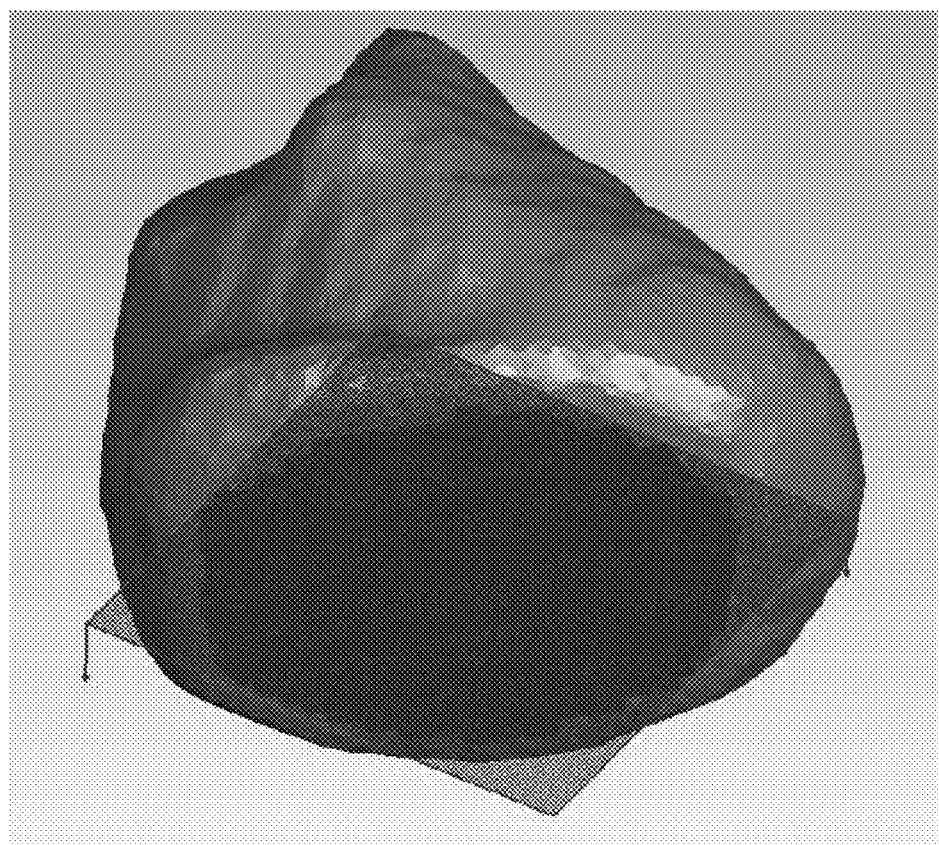
FIG. 3 illustrates a schematic diagram of a surface of enamel-dentine junction with a bottom being separated according to a method embodiment of the disclosure.

Following the obtaining of the curvatures for vertices, the vertices may be clustered based on the curvatures. In an embodiment of the present disclosure, the K-Means algorithm may be used to cluster the vertices of the triangular grid by distance based on the principal curvature values (i.e., Euclidean distance in curvature space). Two objects are first selected at random as centers for clustering, as initial clusters. Then, the data set composed of the principal curvature vector $(k_1, k_2)$ is clustered in each iteration. Particularly, for each object remaining in the data set, the object is reassigned to a closest cluster according to a distance between the object to each of the cluster centers. Having processing all data objects, one iteration is completed, and new cluster centers are obtained. Each of the vertices in the triangular grid will be classified into cluster at the end of the algorithm. The bottom can be separated from the enamel-dentine junction surface with the curvature-based clustering algorithm. FIG. 3 shows a schematic diagram of separating the bottom from the enamel-dentine junction surface with the clustering algorithm. In FIG. 3, the darkest part represents the separated bottom which is composed of a triangular grid.

After removal of the bottom, spherical-parameterization, by means of spherical harmonic analysis, is applied to the surface of the enamel-dentine junction without the bottom at step S300.

In the process, spherical-parameterization of the patch model is first performed with an optimized Control of Area and Length Distortions (CALD) algorithm. Document 9 (Shen L, Makedon F S. Spherical mapping for processing of 3-D closed surfaces. Image and Vision Computing, 24(7): 743-761, 2006) describes the CALD algorithm, which is optimized in the method of the present disclosure.

For the model of the entire triangular grid, the cost $C_a(M, \Psi)$ of area distortion in the parameterization is:

$$C_a(M, \Psi) = \frac{\sum_{t_i \in M} \left[ \max\left( \frac{A(\Psi(t_i))}{A(t_i)}, \frac{A(t_i)}{A(\Psi(t_i))} \right) \times A(\Psi(t_i)) \times \varepsilon(t_i) \right]}{A(\Psi(M))} \quad (6)$$

$M = \{t_i\}$ represents a set of triangles in the original model in the Cartesian coordinate system. $\Psi$ is a reversible map for mapping the triangles M into a grid in the parametric space, i.e., $\Psi(M) = \{\Psi(t_i)\}$. $A(\cdot)$ represents the area of the triangle or the grid in the parametric space.

Here, $\varepsilon(t_i)$ represents a weight and defined with Equation (7):

$$\varepsilon(t_i) = \begin{cases} w & t_i \in B \\ 1.0 & t_i \in T \end{cases} \quad (7)$$

B is a set of triangles at the bottom, and $T = M - B$ is a set of triangles in the original model except the bottom.

Figure 4A:
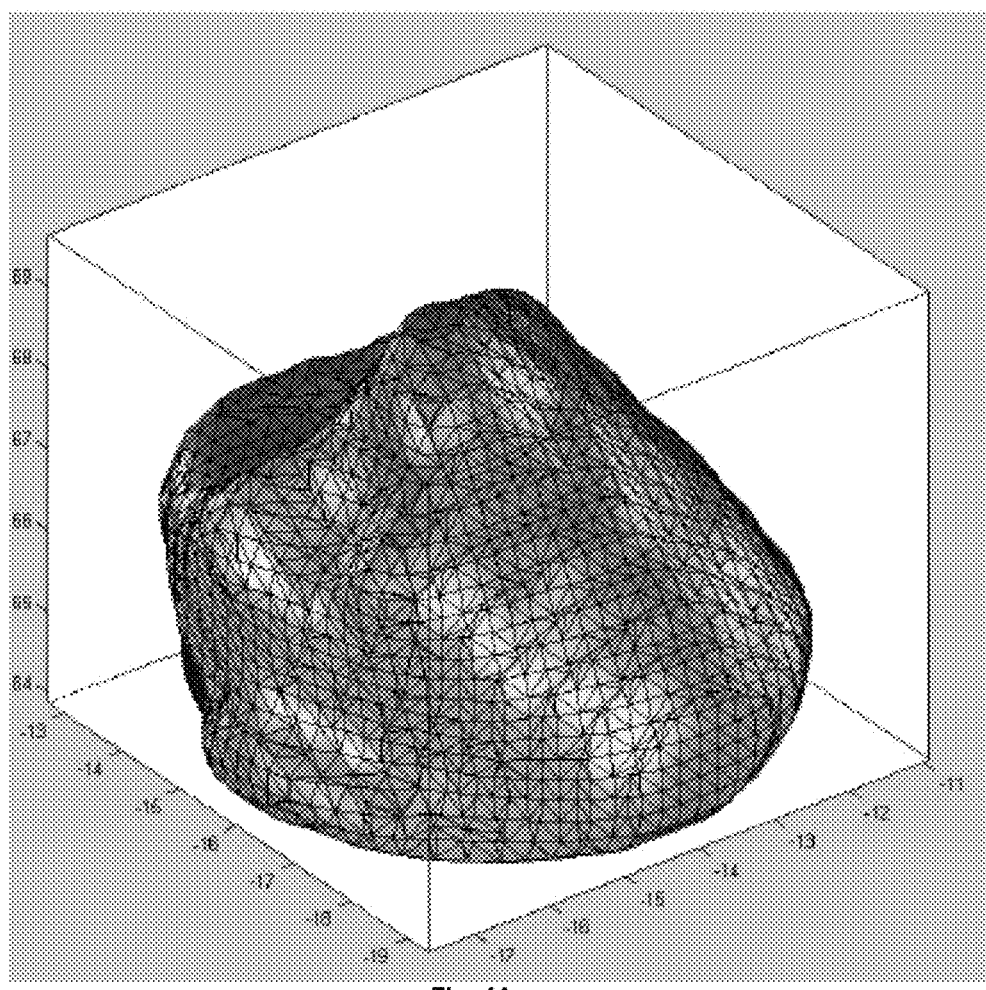
FIGS. 4A, 4B, 4C and 4D illustrate comparison between spherical parameterization according to a method embodiment of the disclosure and spherical parameterization not according to the disclosure.
Figure 4B:
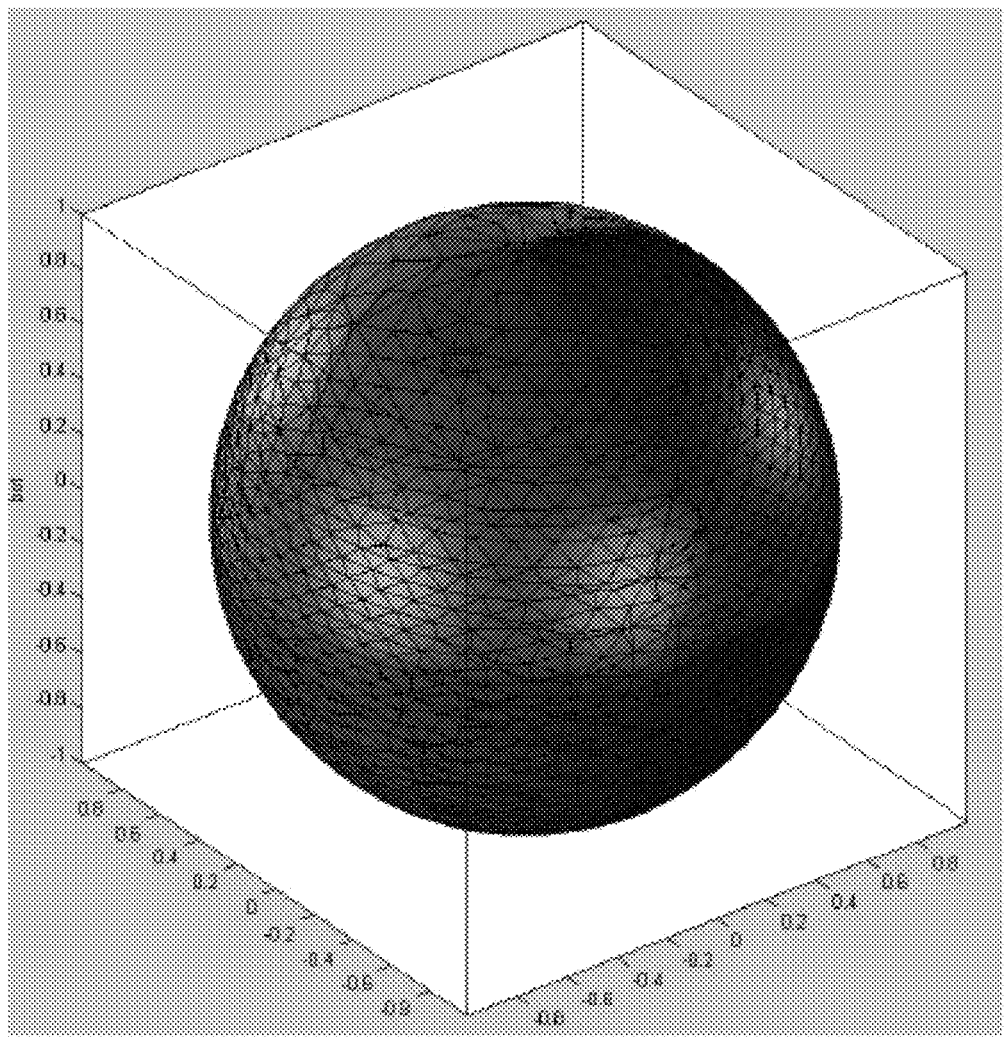
Figure 4C:
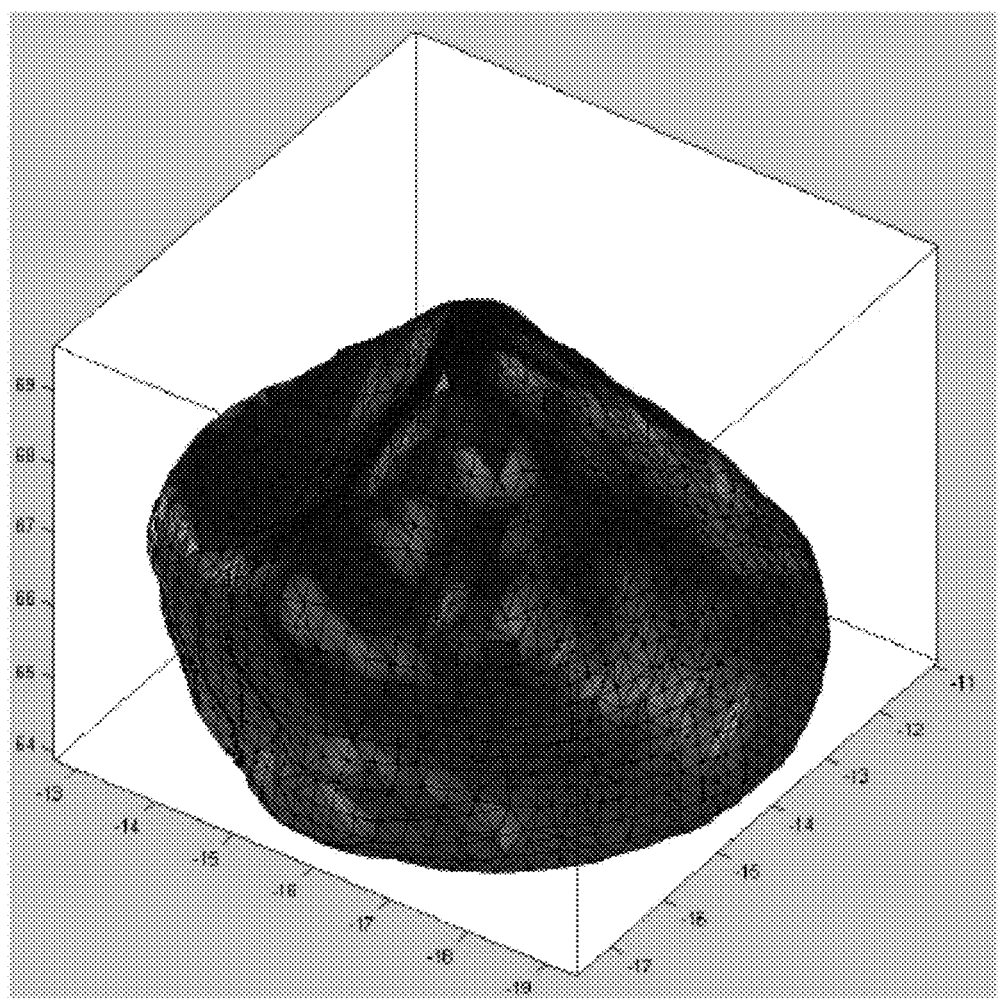
Figure 4D:
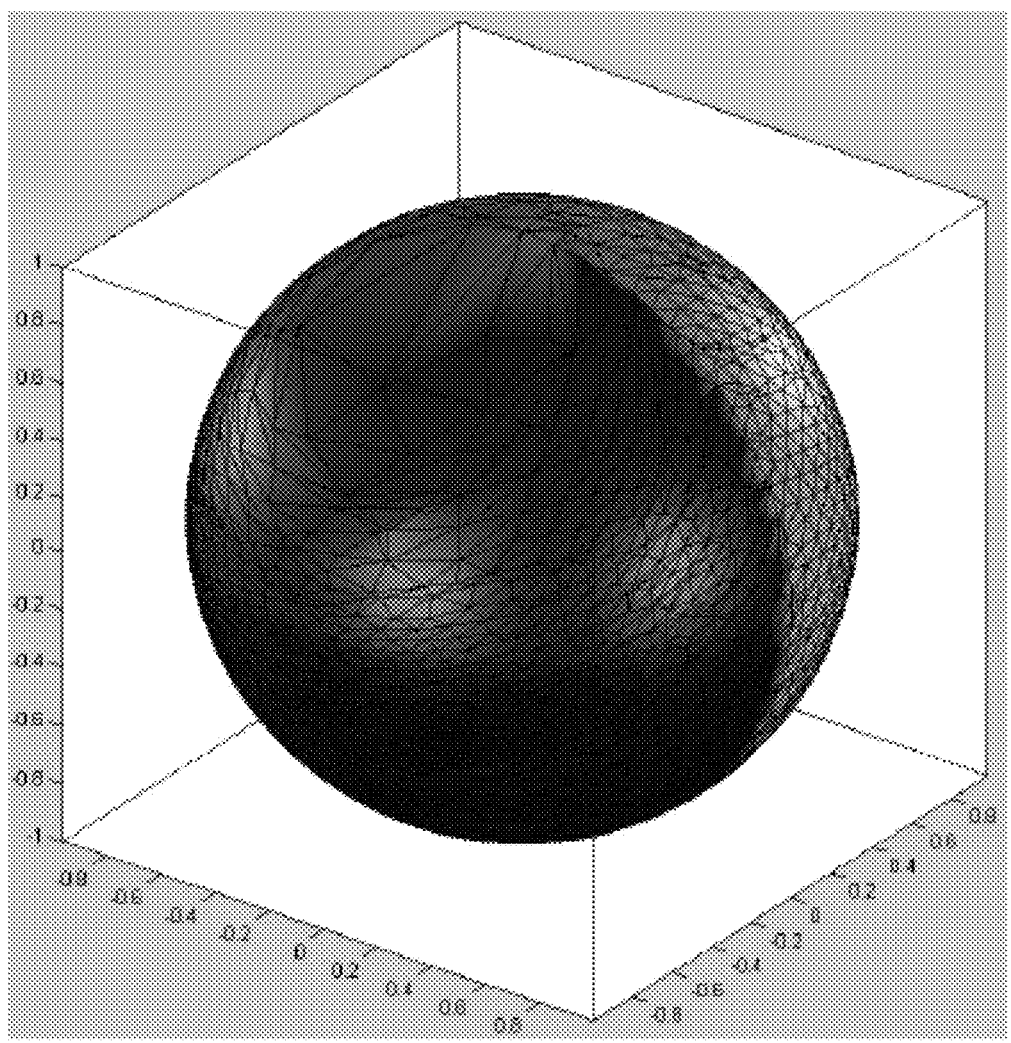

Influence of the bottom area in the parameterization process is reduced by adding the weight $\varepsilon(t_i)$. FIGS. 4A and 4B show results of the spherical parameterization without addition of the weight, and FIGS. 4C and 4D show results of the spherical parameterization with addition of the weight. As can be seen from FIGS. 4A, 4B, 4C and 4D, for the region other than the bottom, the spherical mapping can map the grid of triangles onto a unit sphere in a continuous and uniform manner. For the bottom region, there will be more area distortion in mapping in order to minimize area distortion in the mapping of the non-bottom region.

After the spherical parameterization, a spherical harmonics Fourier expansion is applied to the result of the parameterization to obtain a spherical harmonics function expansion form. The spherical harmonics function $Y_l^m(\theta, \phi)$ ($-l \leq m \leq l$) is a set of functions which are defined in the spherical coordinate system and constitute a set of normalized orthogonal bases on a sphere. The spherical harmonics descriptor is parameterized so that any single-connected curved topology structure is equivalent to a sphere. A point $v(\theta, \phi)$ on the sphere may be represented by a linear combination of the spherical harmonics functions:

$$v(\theta, \phi) = \sum_{l=0}^{\infty} \sum_{m=-l}^{l} c_l^m Y_l^m(\theta, \phi) \quad (8)$$

$c_l^m = (c_{xl}^m, c_{yl}^m, c_{zl}^m)^T$ may be calculated by the least-square estimation. $\hat{c}_l^m$ is an estimate of the original coefficient $c_l^m$. The original function may be restored as follows:

$$\hat{v}(\theta, \phi) = \sum_{l=0}^{L_{max}} \sum_{m=-l}^{l} \hat{c}_l^m Y_l^m(\theta, \phi) \approx v(\theta, \phi)$$

$L_{max}$ is the maximal degree of freedom specified by a user. The larger $L_{max}$ is, the more accurate the restored $\hat{v}(\theta,\phi)$ is.

The parameterization of the model is achieved after spherical harmonics restoration is performed for the vertices of the triangular grid.

Figure 5:
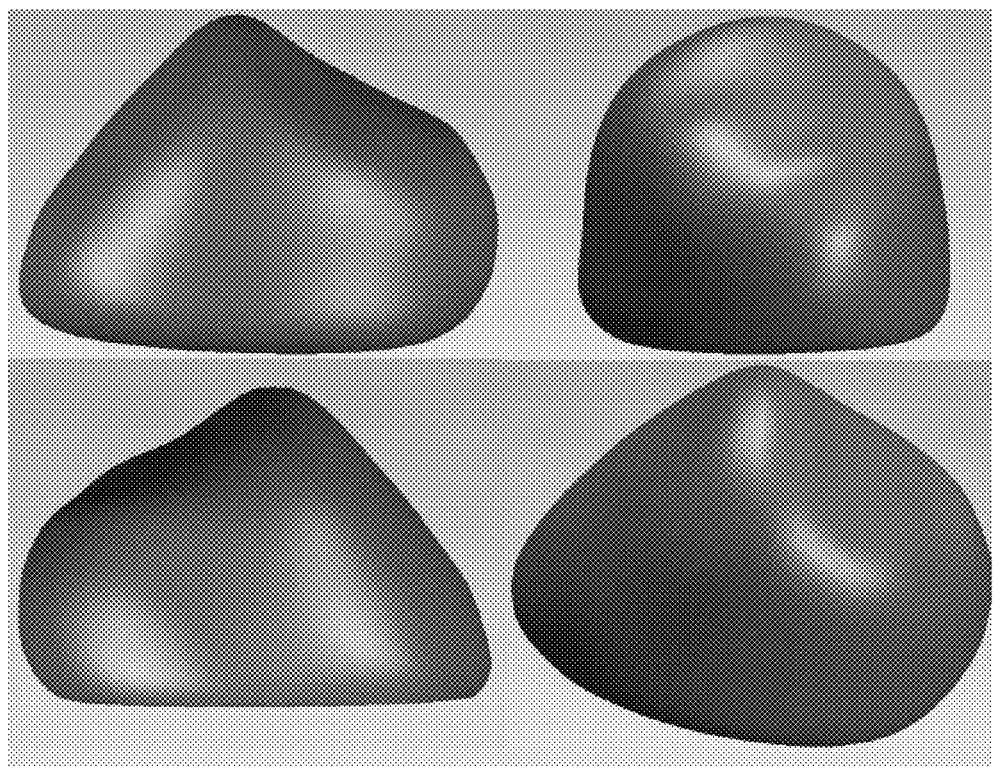
FIG. 5 illustrates a schematic diagram of an average model acquired according to a method embodiment of the disclosure.

Finally at step S400, different samples of the same individual tooth are aligned to acquire a statistical average model for the tooth. FIG. 5 shows the statistical average model of the enamel-dentine junction of a premolar tooth.

In an embodiment of the present disclosure, alignment between the sample model space and the parametric space is performed with the SHREC (SPHARM Registration with Iterative Closest Point) algorithm known from Document 11 (Shen, L., Huang, H., Makdeon, F., Saykin, A. J.: Efficient registration of 3D spharm surface. In: 4th Canadian Conf. on Computer & Robot Vision. (2007) 81-88), and thus correspondence between different sample models may be established. In an example, 45 isolated-tooth samples may be collected to create the statistical average model of the enamel-dentine junction of the first premolar tooth. Use of the SHREC algorithm allows automatic positioning of corresponding mark point sets for the same structure between different individuals.

With the method of the present disclosure, it is possible to create a statistical average model for an unclosed surface. Further, the method can obtain a 3D statistical average model from cone-beam CT image of any other object.

The method of the present disclosure may be implemented in computer software, computer hardware or combination thereof.

The foregoing detailed description has set forth various embodiments of method and apparatus for creating a statistical average model of an enamel-dentine junction by use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the esprit or essence of the disclosure. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present disclosure which is defined by the claims as attached.

What is claimed is:

1. A method of processing image data of a tooth for producing a physical tooth model that simulates structural and optical characteristics of the tooth, the method comprising:
   acquiring, by a Computerized Tomography (CT) machine, CT image data of a tooth;
   segmenting, by a computer, the CT image data to obtain a surface of an enamel-dentine junction of the tooth;
   segmenting, by the computer, the obtained surface using a curvature-based clustering algorithm to remove a bottom of the enamel-dentine junction, wherein a triangular grid model is used to emulate the enamel-dentine junction, and wherein said curvature-based clustering algorithm comprises computing normal vectors at the vertices of the triangular grid model and computing curvatures at the vertices of the triangular grid model based on these normal vectors;
   spherical-parameterizing, by the computer and by means of spherical harmonic analysis, the surface of the enamel-dentine junction after removal of the bottom; and
   aligning, by the computer, different samples of the tooth to create a statistical average model of the enamel-dentine junction;
   wherein the statistical average model of the enamel-dentine junction is used to produce the physical tooth model of the tooth, so that the tooth model simulates structural and optical characteristics of the tooth.

2. The method according to claim 1, wherein the CT image data are segmented using the Level Set algorithm.

3. The method according to claim 2, wherein the clustering algorithm comprises the K-Means algorithm.

4. The method according to claim 3, wherein the spherical-parameterization is performed using an optimized Control of Area and Length Distortions algorithm.

5. The method according to claim 4, wherein the Control of Area and Length Distortions algorithm is optimized by adding weights.

6. The method according to claim 1, further comprising: applying spherical harmonics Fourier expansion on the parameterized surface after the spherical-parameterization.

7. The method according to claim 6, wherein the alignment is performed in a spherical coordinate system.

8. The method according to claim 1, wherein the alignment is performed by means of the SPHARM Registration with Iterative Closest Point (SHREC) algorithm.

9. An apparatus for processing image data of a tooth for producing a physical tooth model that simulates structural and optical characteristics of the tooth, the apparatus comprising:
    a Computerized Tomography (CT) machine configured to acquire CT image data of a tooth;
    a computer configured to create a statistical average model of an enamel-dentine junction of the tooth by
        segmenting the CT image data to obtain a surface of the enamel-dentine junction;
        segmenting the obtained surface using a curvature-based clustering algorithm to remove a bottom of the enamel-dentine junction, wherein a triangular grid model is used to emulate the enamel-dentine junction, and wherein said curvature-based clustering algorithm comprises computing normal vectors at the vertices of the triangular grid model and computing curvatures at the vertices of the triangular grid model based on these normal vectors;
        spherical-parameterizing, by means of spherical harmonic analysis, the surface of the enamel-dentine junction after removal of the bottom; and
        aligning different samples of the tooth to obtain the statistical average model;
wherein the statistical average model of the enamel-dentine junction is used to produce the physical tooth model of the tooth, so that the tooth model simulates structural and optical characteristics of the tooth based.

* * * * *